US008226575B2

(12) United States Patent
Levy

(10) Patent No.: US 8,226,575 B2
(45) Date of Patent: Jul. 24, 2012

(54) BIOPSY NEEDLE ASSEMBLIES

(75) Inventor: Michael J. Levy, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 234 days.

(21) Appl. No.: 12/780,596

(22) Filed: May 14, 2010

(65) Prior Publication Data

US 2010/0298736 A1 Nov. 25, 2010

Related U.S. Application Data

(60) Provisional application No. 61/178,714, filed on May 15, 2009.

(51) Int. Cl.
A61B 10/00 (2006.01)
A61B 17/32 (2006.01)

(52) U.S. Cl. .................................... 600/566; 606/167

(58) Field of Classification Search .................. 600/562, 600/564–568; 606/167, 170
See application file for complete search history.

(56) References Cited

U.S. PATENT DOCUMENTS

| 4,235,244 | A | * | 11/1980 | Abele et al. | 600/562 |
| 6,440,153 | B2 | * | 8/2002 | Cragg et al. | 606/213 |
| 6,569,105 | B1 | * | 5/2003 | Kortenbach et al. | 600/562 |
| 7,662,128 | B2 | | 2/2010 | Salcudean et al. | |

OTHER PUBLICATIONS

Al-Khafaji et al., "Fine-needle aspiration of 154 parotid masses with histologic correlation: ten-year experience at the University of Texas M. D. Anderson Cancer Center," *Cancer*, 1998, 84(3):153-159.
Amrikachi et al., "Accuracy of fine-needle aspiration of thyroid," *Arch Pathol Lab Med.*, 2001, 125(4):484-488.
Anand et al., "Endoscopic ultrasound guided fine needle aspiration of non-pancreatic lesions: an institutional experience," *J Clin Pathol.*, 2007, 60(11):1254-1262.
Annema et al., "Towards a minimally invasive staging strategy in NSCLC: analysis of PET positive mediastinal lesions by EUS-FNA," *Lung Cancer*, 2004, 44(1):53-60.
Belsley et al., "Serous cystadenoma of the pancreas: limitations and pitfalls of endoscopic ultrasound-guided fine-needle aspiration biopsy," *Cancer*, 2008, 114(2):102-110.
Bodner et al., "Aspiration biopsy of the prostate," *World J Urol.*, 1987, 5:62-64.
Chang et al., "The clinical utility of endoscopic ultrasound-guided fine-needle aspiration in the diagnosis and staging of pancreatic carcinoma," *Gastrointest Endosc.*, 1997, 45(5):387-393.
Crannen et al., "Endoscopic ultrasound guided fine-needle aspiration and 18FDG-positron emmission tomography in the evaluation of patients with non-small cell lung cancer," *Interact Cardiovasc Thorac Surg.*, 2007, 6(4):433-436.
Deshpande et al., "Endoscopic ultrasound guided fine needle aspiration biopsy of autoimmune pancreatitis: diagnostic criteria and pitfalls," *Am J Surg Pathol.*, 2005, 29(11):1464-1471.

(Continued)

Primary Examiner — Max Hindenberg
Assistant Examiner — Emily Lloyd
(74) Attorney, Agent, or Firm — Fish & Richardson P.C.

(57) ABSTRACT

This document provides needle biopsy systems and methods for obtaining tissue biopsies. In various embodiments, the systems and methods provided can inhibit needle contamination by unwanted tissue or cells and/or regulate a negative pressure to assist sampling of target tissue or cells.

21 Claims, 14 Drawing Sheets

OTHER PUBLICATIONS

Eloubeidi et al., "Endoscopic ultrasound-guided fine needle aspiration of mediastinal lymph node in patients with suspected lung cancer after positron emission tomography and computed tomography scans," *Ann Thorac Surg.*, 2005, 79(1):263-268.

Eloubeidi et al., "Impact of staging transesophageal EUS on treatment and survival in patients with non-small-cell lung cancer," *Gastrointest Endosc.*, 2008, 67(2):193-198.

Fernandez-Esparrach et al., "Transesophageal ultrasound-guided fine needle aspiration improves mediastinal staging in patients with non-small cell lung cancer and normal mediastinum on computed tomography," *Lung Cancer*, 2006, 54(1):35-40.

Friedlander et al., "Diagnostic pitfalls in fine needle aspiration biopsy of the spleen," *Diagn Cytopathol.*, 2008, 36(2):69-75.

Fritscher-Ravens et al., "Mediastinal lymphadenopathy in patients with or without previous malignancy: EUS-FNA-based differential cytodiagnosis in 153 patients," *Am J Gastroenterol.*, 2000, 95(9):2278-2284.

Haberal et al., "The value of fine-needle aspiration biopsy in salivary gland tumors," *International Congress Series 1240*, 2003, 629-634.

Hautmann et al., "Detection rate of histologically insignificant prostate cancer with systematic sextant biopsies and fine needle aspiration cytology," *J Urol.*, 2000, 163(6):1734-1738.

Jani et al., "Endoscopic ultrasound-guided fine-needle aspiration for diagnosis of solid pseudopapillary tumors of the pancreas: a multicenter experience," *Endoscopy.* 2008, 40(3):200-203.

Jhala et al., "Endoscopic ultrasound-guided fine-needle aspiration. A cytopathologist's perspective," *Am J Clin Pathol.*, 2003, 120(3):351-367.

Kocjan et al., "Percutaneous fine needle aspiration cytology of the pancreas: advantages and pitfalls," *J Clin Pathol.*, 1989, 42(4):341-347.

Kramer et al., "Analysis of cytological specimens from mediastinal lesions obtained by endoscopic ultrasound-guided fine-needle aspiration," *Cancer*, 2006, 108(4):206-211.

Kulesza and Eltoum, "Endoscopic ultrasound-guided fine-needle aspiration: sampling, pitfalls, and quality management," *Clin Gastroenterol Hepatol.*, 2007, 5(11):1248-1254.

Larghi et al., "EUS followed by EMR for staging of high-grade dysplasia and early cancer in Barrett's esophagus," *Gastrointest Endosc.*, 2005, 62(1):16-23.

Lee et al., "Sonographically guided fine needle aspiration of thyroid nodule: discrepancies between cytologic and histopathologic findings," *J Clin Ultrasound*, 2008, 36(1):6-11.

Levy et al., "Prospective Cytologic Assessment of Gastrointestinal Luminal EUS: A Potential Source of False-Positive FNA and Needle Tract Seeding," *Am. J Gastroenterology*, 2010, 1311-1318.

Logrono, "Primer: cytopathology for the clinician—how to interpret the results of aspiration cytology," *Nat Clin Pract Gastroenterol Hepatol.*, 2005, 2(10):484-491.

Mahbod and Tagreshi, "Fine needle aspiration cytology in diagnosis of nonthyroidal neck masses," *Acta Medica Iranica*, 2002, 40(1):49-51.

Masoom et al., "Renal FNA-based typing of renal masses remains a useful adjunctive modality: evaluation of 31 renal masses with correlative histology," *Cytopathology*, 2009, 20(1):50-55.

Mazeh et al., "Cytohistologic correlation of thyroid nodules," *Am J Surg.*, 2007, 194(2):161-163.

Mcdonough et al., "Does FDG-PET add information to EUS and CT in the initial management of esophageal cancer? A prospective single center study," *Am J Gastroenterol.*, 2008, 103(3):570-574.

Micames et al., "Endoscopic ultrasound-guided fine-needle aspiration for non-small cell lung cancer staging: A systematic review and metaanalysis," *Chest*, 2007, 131(2):539-548.

Mishra, "DNA analysis of cells obtained from endoscopic ultrasound-fine needle aspiration in pancreatic adenocarcinoma: Fool's Gold, Pandora's Box, or Holy Grail?" *Am J Gastroenterol.*, 2006, 101(11):2501-2503

Mitsuhashi et al., "Endoscopic ultrasound-guided fine needle aspiration of the pancreas: cytomorphological evaluation with emphasis on adequacy assessment, diagnostic criteria and contamination from the gastrointestinal tract," *Cytopathology*, 2006, 17(1):34-41.

Nodit et al., "Improving the quality of cytology diagnosis: root cause analysis for errors in bronchial washing and brushing specimens," *Am J Clin Pathol.*, 2005, 124(6):883-892.

Overholt et al., "Five-year efficacy and safety of photodynamic therapy with Photofrin in Barrett's high-grade dysplasia," *Gastrointest Endosc.*, 2007, 66(3):460-468.

Pech et al., "The impact of endoscopic ultrasound and computed tomography on the TNM staging of early cancer in Barrett's esophagus," *Am J Gastroenterol.*, 2006, 101(10):2223-2229.

Pelllise Urquiza et al. "Endoscopic ultrasound-guided fine needle aspiration: predictive factors of accurate diagnosis and cost-minimization analysis of on-site pathologist," *Gastroenterol Hepatol.*, 2007, 30(6):319-324.

Pitman, "Fine needle aspiration biopsy of the pancreas," *Pancreatitis—Chp 5*, 1999, pp. 31-51.

Policarpio-Nicolas and Wick, "False-positive interpretations in respiratory cytopathology: exemplary cases and literature review," *Diagn Cytopathol.*, 2008, 36(1):13-19.

Rampado et al., "Endoscopic Ultrasound: Accuracy in Staging Superficial Carcinomas of the Esophagus," *Ann Thorac Surg.*, 2008, 85(1):251-256.

Ramzy, "Gastrointestinal Tract," *Clinical cytopathology and aspiration biopsy*, 2000, 2nd Ed. McGraw-Hill Professional, pp. 285-290.

Sautereau et al., "Value of sonographically guided fine needle aspiration biopsy in evaluating the liver with sonographic abnormalities," *Gastroenterology*, 1987, 93(4):715-718.

Savides et al., "EUS-guided FNA diagnostic yield of malignancy in solid pancreatic masses: a benchmark for quality performance measurement," *Gastrointest Endosc.*, 2007, 66(2):277-282.

Schwartz et al., "The rate of false-positive results with EUS-guided fine-needle aspiration," *Gastrointest Endosc.*, 2002, 56(6):868-872.

Schwerk et al., "Ultrasound guided fine-needle biopsies in pancreatic and hepatic neoplasms," *Gastrointest Radiol.*, 1983, 8(3):219-225.

Sears and Dupont, "A steerable needle technology using curved concentric tubes," Proc. of the 2006 IEEE/RSJ International Conf. on Intelligent Robots and Systems, Beijing, China, Oct. 9-15, 2006, pp. 2850-2856.

Shami et al., "Clinical impact of conventional endosonography and endoscopic ultrasound-guided fine-needle aspiration in the assessment of patients with Barrett's esophagus and high-grade dysplasia or intramucosal carcinoma who have been referred for endoscopic ablation therapy," *Endoscopy*, 2006, 38(2):157-161.

Stanley, "False-positive diagnoses in exfoliative cytology," *Am J Clin Pathol.*, 1995, 104:117-119.

Torp-Pedersen et al., "US-guided fine needle biopsy of solid renal masses—comparison of histology and cytology," *Scand J Urol Nephrol Suppl.*, 1991, 137:41-43.

Tse et al., "Fine needle aspiration cytology of papillary lesions of the breast: how accurate is the diagnosis?" *J Clin Pathol.*, Aug. 2008, 61(8):945-949.

Vazquez-Sequeiros et al., "Impact of lymph node staging on therapy of esophageal carcinoma," *Gastroenterology*, 2003, 125(6):1626-1635.

Wang and Sampliner, "Practice Parameters Committee of the American College of Gastroenterology. Updated guidelines 2008 for the diagnosis, surveillance and therapy of Barrett's esophagus," *Am J Gastroenterol.*, 2008, 103(3):788-797.

Weidner et al., "Peptic ulceration with marked epithelial atypia following hepatic arterial infusion chemotherapy. A lesion initially misinterpreted as carcinoma," *Am J Surg Pathol.*, 1983, 7(3):261-268.

Wiersema et al., "Endosonography-guided fine-needle aspiration biopsy: diagnostic accuracy and complication assessment," *Gastroenterology*, 1997, 112(4):1087-1095.

Wilson et al., "Diagnosis of solid pancreatic masses by endoscopic ultrasound-guided fine-needle aspiration," *Intern Med J.*, 2009, 39(1):32-37.

Yamasita et al., "Hepatic sclerosing hemangioma mimicking a metastatic liver tumor: report of a case," *Surg Today*, 2000, 30(9):849-852.

Zardawi, "Renal fine needle aspiration cytology," *Acta Cytol.*, 1999, 43(2):184-190.

\* cited by examiner

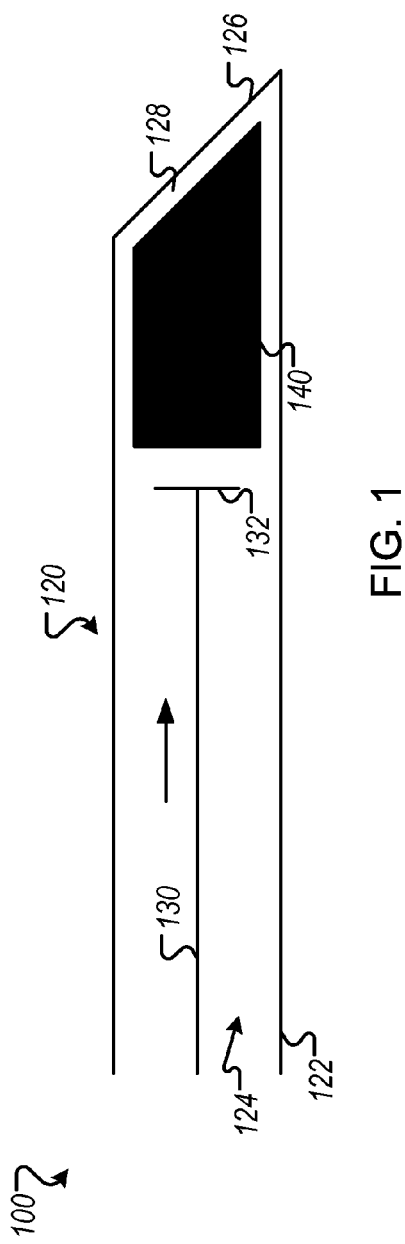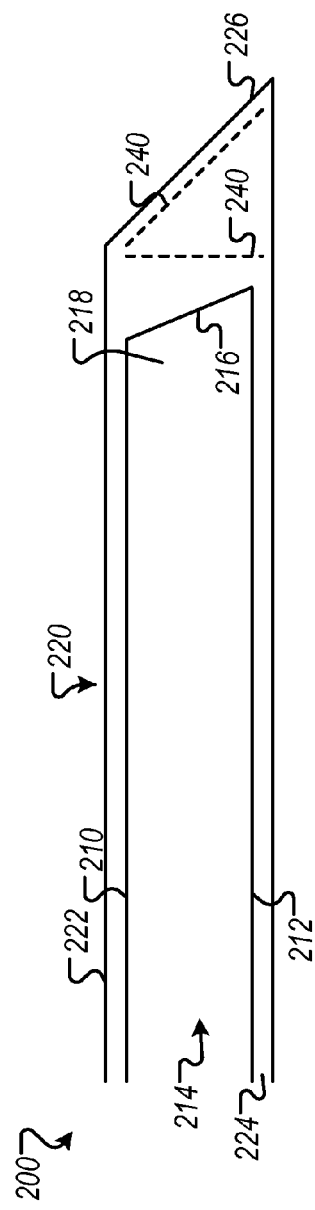

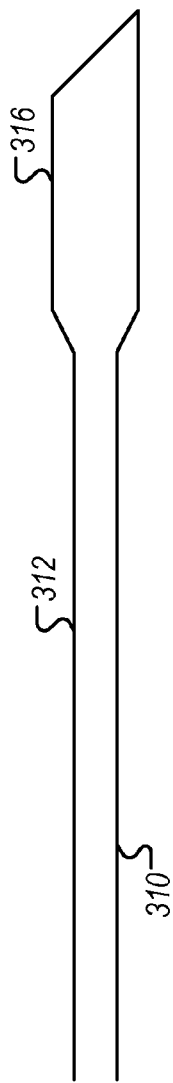
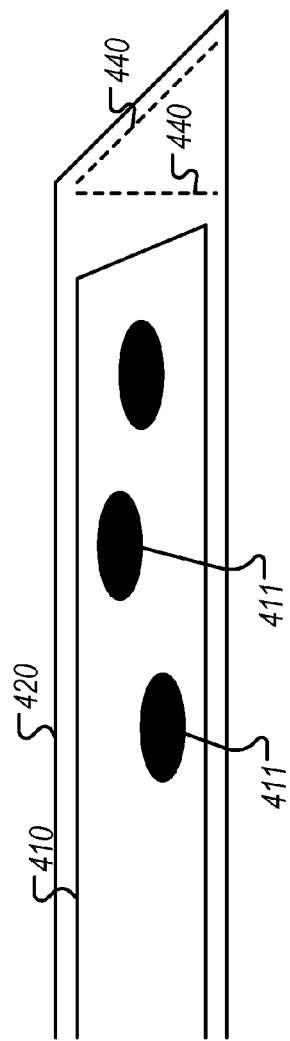

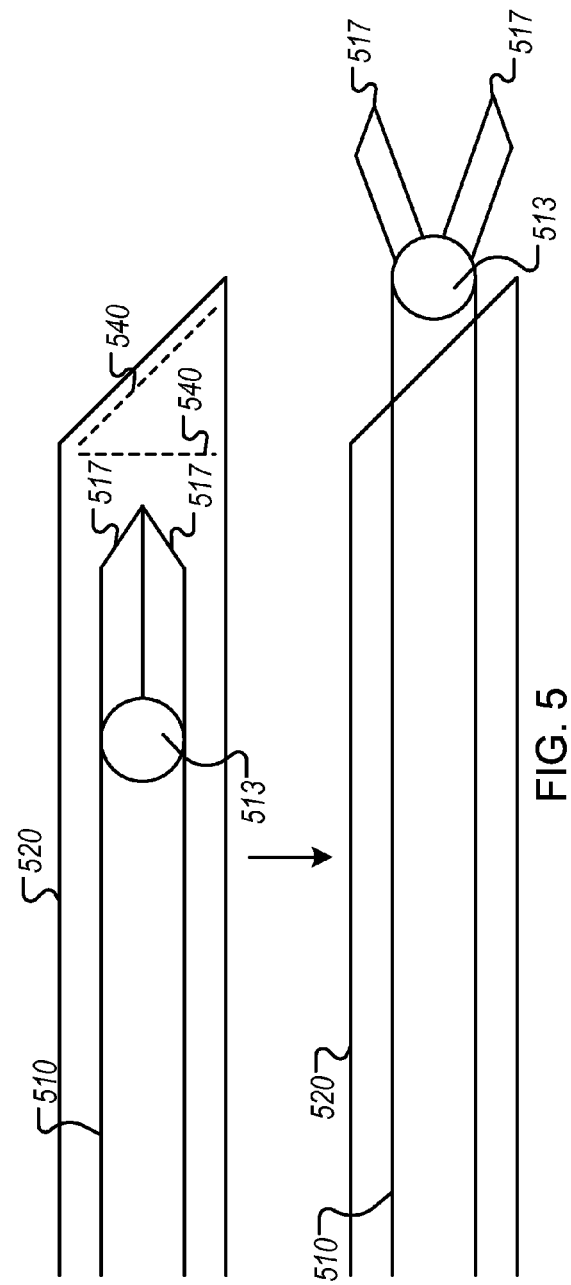
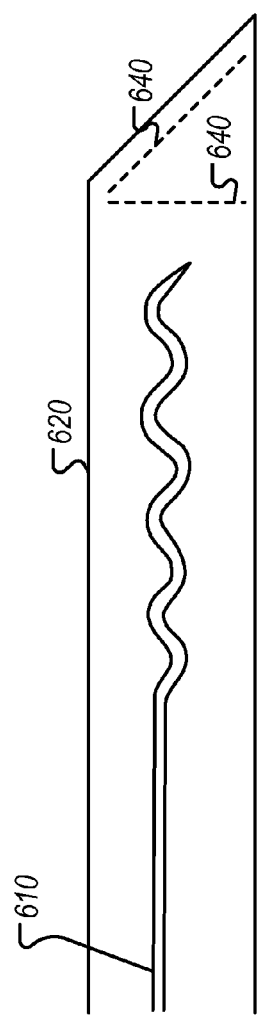
FIG. 5
FIG. 6

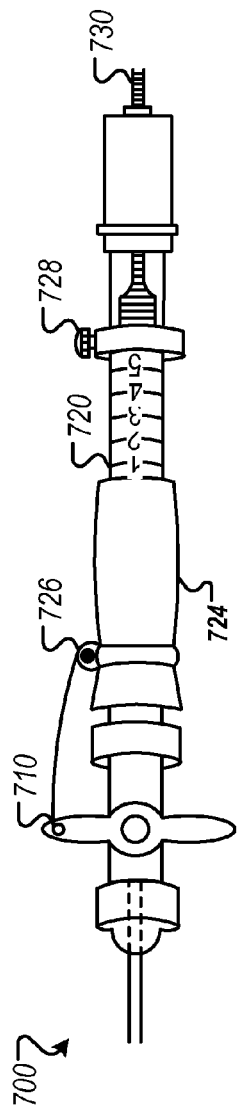
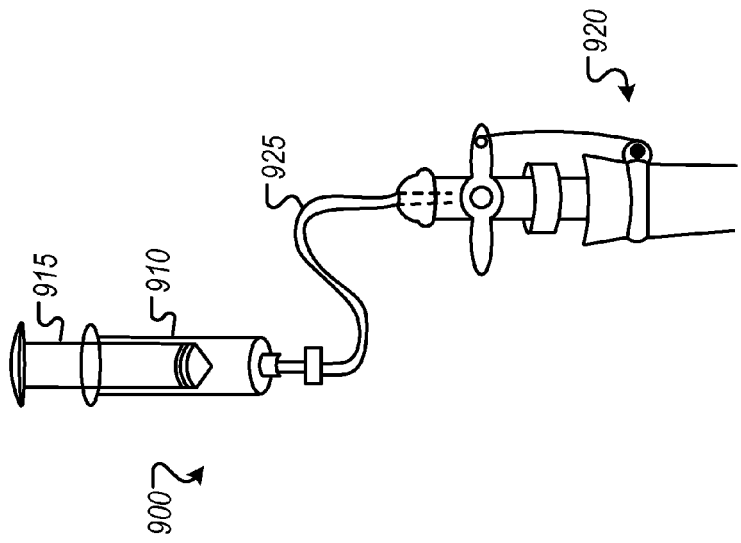
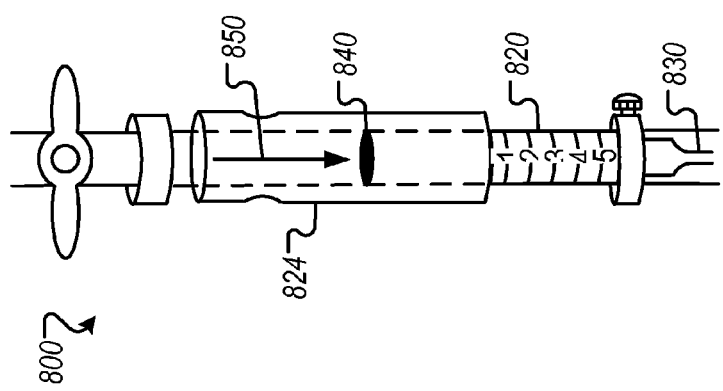

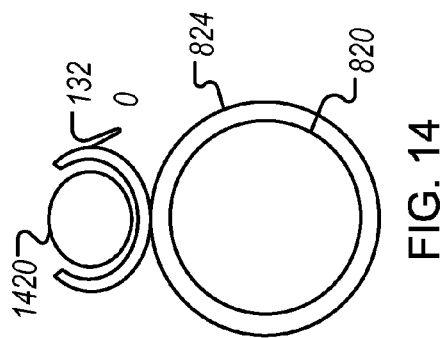
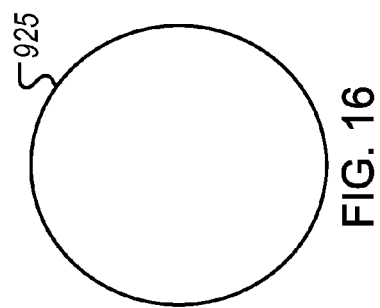
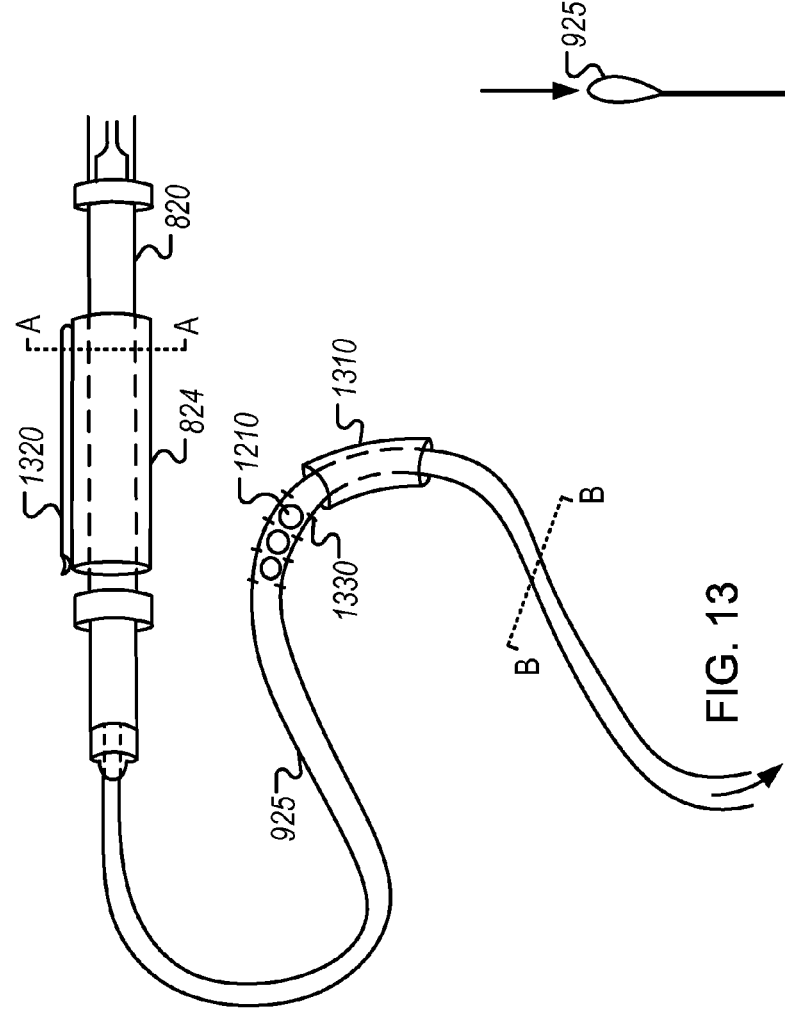

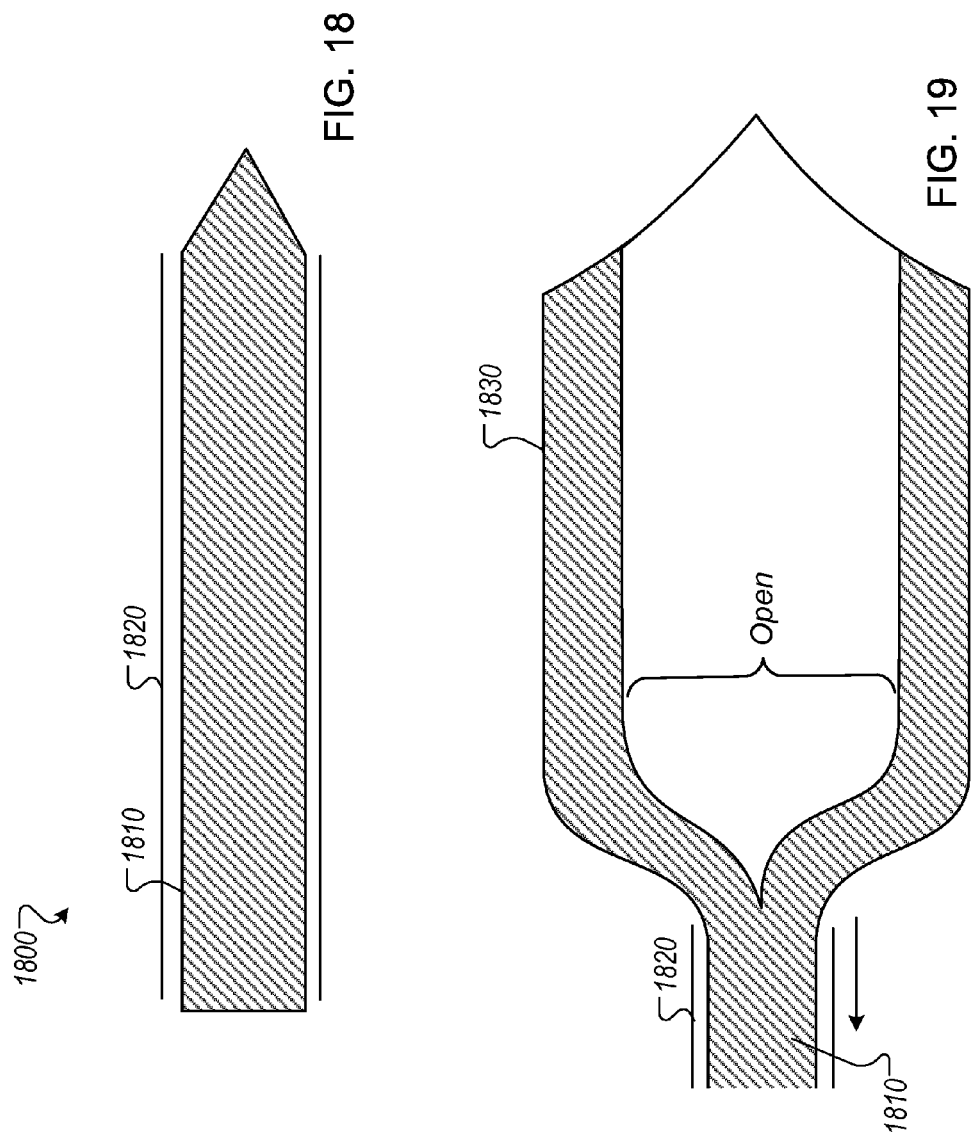

BIOPSY NEEDLE ASSEMBLIES

CROSS-REFERENCE TO RELATED APPLICATIONS

This application is claims the benefit of priority to U.S. Provisional Application Ser. No. 61/178,714, filed May 15, 2009. The disclosures of the prior application is considered part of (and is incorporated by reference in) the disclosure of this application.

TECHNICAL FIELD

This document relates to biopsy needle assemblies and needle biopsy processes (e.g., endoscopic ultrasound-guided fine needle aspiration).

BACKGROUND

Ultrasound-guided fine needle aspiration is a medical procedure that can be used to obtain a sample of tissue for examination. This procedure can allow for cytologic confirmation of imaging findings and is often performed during the evaluation of luminal or extraluminal gastrointestinal and non-gastrointestinal disorders.

SUMMARY

This document provides systems and methods for obtaining tissue biopsies. For example, this document provides biopsy needle assemblies that can be used to obtain tissue, fluid, or cells from a mammal.

For patients undergoing endosonography, the rate of false positive fine needle aspiration can be over 7%, and 26% for esophageal lymph node fine needle aspiration. These rates appear to be consistent with those for fine needle aspiration procedures performed via other modalities and routes including percutaneously guided fine needle aspiration of the thyroid, breast, kidney, pancreas, liver salivary glands, and more.

While cytopathologist errors of interpretation may account for some of the false positive exams, the majority can result from contamination by epithelial cells, dysplastic cells, mesothelial or inflammatory cells that may be collected during transmural needle passage. The translocation of cells from an unintended site into the site of biopsy can have several implications. For example, false positive fine needle aspiration results may lead to inappropriate and often unnecessary therapies that can include chemotherapy, radiation therapy, and even surgical resection. As a result, patients can suffer the medical, physical, and psychological effect of these unnecessary interventions. Also, the cell translocation may not only lead to false positive examinations, but can also implant tumor cells along the tract of the needle (needle tract seeding) as well as deposit tumor cells into the biopsy site. The presence of needle tract seeding can serve as a site of cancer recurrence (actually unappreciated residual tumor cells). In addition, there may be concern that this process can lead to more rapid overall disease recurrence, which may not represent recurrence, but deposition of cancer cells into previously "sterile" sites thereby negatively impacting patient care and outcomes.

The biopsy needle assemblies provided herein can include a barrier to prevent or inhibit the collection of cancer (or pre-neoplastic) cells from an unwanted site while the needle assemblies are advanced to a biopsy site during a biopsy procedure. The biopsy needle assemblies also can be regulated to a negative pressure to assist biopsy sampling (e.g., tissue acquisition) when the barrier is removed upon the needle assemblies reaching a desired biopsy site.

In general, one aspect of this document features a biopsy needle assembly comprising (a) a needle having a body portion and a tip portion, the body portion having a channel and the tip portion having an opening; (b) a plug located within the opening at the tip portion and configured to seal the channel; and (c) a slideable stylet located within the channel at the body portion and configured to push the plug out of the opening. The biopsy needle assembly can further comprise a pressurization device configured to regulate a pressure within the channel to a negative level during a biopsy procedure. The pressurization device can comprise a syringe, a suction gun, or a wall mounted pressure unit.

In another aspect, this document features a method of obtaining a tissue biopsy comprising (a) providing a biopsy needle assembly comprising (i) a needle having a body portion and a tip portion, the body portion having a channel and the tip portion having an opening; (ii) a plug located within the opening at the tip portion and configured to seal the channel; and (iii) a slideable stylet located within the channel at the body portion and configured to push the plug out of the opening; (b) advancing the biopsy needle assembly to a desired biopsy site; (c) actuating the slideable stylet to push the plug out of the needle; and (d) acquiring a tissue biopsy through the opening and the channel.

In another aspect, this document features a biopsy needle assembly comprising (a) an outer carrier needle having a body portion and a tip portion, the body portion having a channel and the tip portion having an opening; (b) a membrane located within the opening at the tip portion and configured to seal the channel; and (c) a slideable inner biopsy device located within the channel at the body portion and configured to pierce the membrane. The inner biopsy device can comprise an inner biopsy needle having a body portion and a tip portion, wherein the body portion has a channel and the tip portion has an opening, and wherein the inner biopsy needle is configured to acquire a tissue biopsy through the opening and the channel. The body portion of the outer carrier needle can have a smaller diameter than the tip portion of the outer carrier needle. The body portion of the inner biopsy needle can have a smaller diameter than the tip portion of the inner biopsy needle. The inner biopsy needle can include one or more holes to assist tissue biopsy acquisition. The biopsy needle assembly can further comprise a pressurization device configured to regulate a pressure within the channel of the inner biopsy needle to a negative level during a biopsy procedure. The pressurization device can comprise a syringe, a suction gun, or a wall mounted pressure unit. The inner biopsy device can comprise an inner biopsy forceps configured to cut a target tissue. The inner biopsy device can comprise an inner coring needle configured to core a target tissue.

In another aspect, this document features a method of obtaining a tissue biopsy comprising (a) providing a biopsy needle assembly comprising (i) an outer carrier needle having a body portion and a tip portion, the body portion having a channel and the tip portion having an opening; (ii) a membrane located within the opening at the tip portion and configured to seal the channel; and (iii) a slideable inner biopsy device located within the channel at the body portion and configured to pierce the membrane; (b) actuating the slideable inner biopsy device to pierce the membrane; and (c) acquiring a tissue biopsy using the inner biopsy device.

In another aspect, this document features a needle biopsy system comprising (a) a pressurization device having a channel and configured to create a negative pressure within the channel; (b) a handle having a channel and a piston configured to advance or retract a biopsy needle; and (c) a valve configured to separate the channel of the pressurization device and the channel of the handle when the valve is a closed position and to allow fluid communication between the channel of the pressurization device and the channel of the handle when the valve is in an open position; wherein the valve is attached to the handle piston so that an advancement of the piston simultaneously causes an advancement of the biopsy needle and a gradual opening of the valve. The pressurization device can comprise a syringe, a suction gun, or a wall mounted pressure unit. The biopsy needle can comprise a biopsy needle assembly comprising a needle having a plug located at a tip end to seal the needle and a slideable stylet located inside the needle to push the plug out of the needle. The biopsy needle can comprise a needle assembly comprising an outer carrier needle having a membrane located at a tip end to seal the outer carrier needle and a slideable inner biopsy device located inside the outer carrier needle to pierce the membrane. The slideable inner biopsy device can comprise an inner biopsy needle configured to acquire a tissue biopsy through the inner biopsy needle. The outer carrier needle can comprise a body and a tip potion that has a larger diameter than the body portion. The inner biopsy needle can have a body portion and a tip portion that has a larger diameter than the body portion. The inner biopsy needle can include one or more holes to facilitate tissue sampling. The inner biopsy device can comprise an inner biopsy forceps configured to cut a target tissue. The inner biopsy device can comprise an inner coring needle configured to core a target tissue.

In another aspect, this document features a biopsy cable comprising a shape memory material configured to change shape and/or size in a human body.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 shows an exemplary biopsy needle assembly having a plug.

FIG. 2 shows an exemplary biopsy needle assembly having a membrane.

FIG. 3 shows an exemplary needle having a flexible shaft and a rigid head

FIG. 4 shows an exemplary biopsy needle assembly having an inner biopsy needle with holes.

FIG. 5 shows an exemplary biopsy needle assembly having an inner biopsy forceps.

FIG. 6 shows an exemplary biopsy needle assembly having an inner coring needle.

FIG. 7 shows an exemplary needle biopsy system to control negative pressure actuation using a valve.

FIG. 8 shows an exemplary needle biopsy system to control negative pressure actuation using a membrane.

FIG. 9 shows an exemplary use of a syringe to induce negative pressure in a biopsy system.

FIG. 13 shows an exemplary needle biopsy system to control negative pressure actuation using holes present in the tube in combination with a slider.

FIG. 14 is a cross sectional view along the A-A line of FIG. 13.

FIG. 15 is a cross sectional view along the B-B line of FIG. 13 with the tube in a closed position.

FIG. 16 is a cross sectional view along the B-B line of FIG. 13 with the tube in an open position.

FIG. 18 shows an exemplary biopsy needle assembly having an expandable inner biopsy needle.

FIG. 19 shows the exemplary biopsy needle assembly of FIG. 18 with the expandable inner biopsy needle in the expanded position.

Like reference symbols in the various drawings indicate like elements.

DETAILED DESCRIPTION

Figure 10:
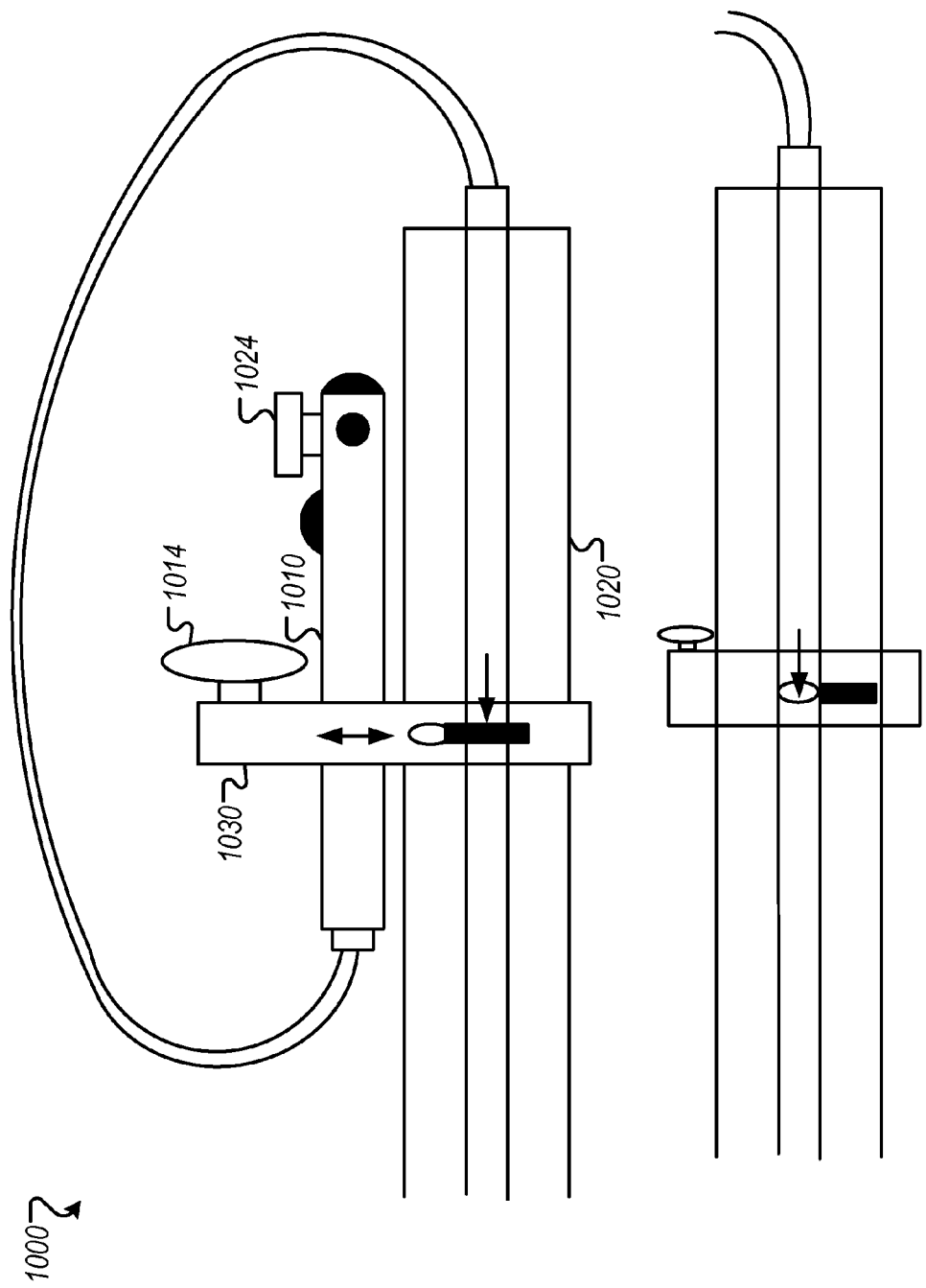
FIG. 10 shows an exemplary use of an inflator for controlled release of negative pressure.

The biopsy needle assemblies provided herein can reduce the risk of cell contamination during a biopsy procedure. The needle assemblies can have a barrier that may be located at a needle tip end, within a needle handle, or other suitable positions to prevent unwanted cells or tissue from entering into the needle assemblies during needle placement. In some cases, the interior of the needle assemblies can be maintained at a negative pressure during a biopsy procedure to automatically collect a target tissue when the barrier is removed at a biopsy site. The biopsy needle assemblies provided herein can be used in various needle biopsy systems to acquire tissue via various routes and techniques (e.g., endoscopic ultrasound-guided fine needle aspiration, endobronchial ultrasound, percutaneous routes/methods, or during surgery). This document provides various embodiments of biopsy needle assemblies that can inhibit cell contamination and/or control negative pressure actuation during a biopsy procedure.

Referring now to FIG. 1, an exemplary biopsy needle assembly 100 can include a needle 120 that can have a body 122 and a tip 126. The needle body 122 can have a channel 124 through which the needle assembly 100 can collect biopsy tissue or cells. A slideable stylet 130 can be located within the needle channel 124. In some cases, stylet 130 can have a tip 132 (e.g., a rounded or beveled tip). In some cases, another needle (not shown) can be used instead of the stylet 130. Needle tip 126 can have an opening 128 for biopsy tissue or cells sampling. Needle tip 126 can allow needle 120 to penetrate into various tissues. In some cases, needle 120 can be a metal needle that can be made of stainless steel or Nitinol. In some cases, needle 120 (or any needle provided herein) can be a combination of a stainless steel shaft with a nitinol (or other shape memory alloy) distal tip. A plug 140 can be included at tip region 126 of needle 120 to seal needle channel 124. In some cases, plug 140 can be made of a biodegradable polymer. Representative examples of suitable biodegradable polymers include, without limitation, polydioxanone, polycaprolactone, polygluconate, polylactic acid-polyethylene oxide copolymers, modified cellulose, collagen, poly(hydroxybutyrate), polyanhydride, polyphosphoester, poly (amino acids), poly-L-lactide, poly-D-lactide, polyglycolide, poly(alpha-hydroxy acid), and combinations thereof.

As needle 120 advances to a biopsy site, plug 140 can inhibit unwanted tissue or cells from contaminating needle channel 124. When needle 120 reaches the biopsy site, stylet 130 can be actuated to push plug 140 out of needle tip opening 128. Stylet 130 can then be retracted from needle channel 124, and biopsy tissue or cells can be sampled through needle tip opening 128 and needle channel 124. In some implementations, during a biopsy procedure a pressurization device (not shown), e.g., a syringe, suction gun, a wall mounted pressure unit, or the like, can be used to regulate a pressure in needle channel 124 to a negative level (e.g., vacuum) such that needle assembly 100 can automatically collect biopsy tissue or cells as soon as plug 140 is pushed out of needle tip 126. In some cases, a free-standing machine that includes a trap can be used to collect a sample (e.g., a fluid or secretion). In some implementations, a pressurization device (e.g., a syringe (not shown)) can be attached to needle 120 so that, after plug 140 is pushed out of needle 120, biopsy tissue or cells can be sampled by actuating the pressurization device (e.g., by pulling a plunger of the syringe) to create a low pressure in needle channel 124.

Referring now to FIG. 2, an exemplary biopsy needle assembly 200 can include an outer carrier needle 220 that can have a body 222 and a tip 226. Carrier needle body 222 can have a channel 224 within which an inner biopsy needle 210 can be located. Carrier needle tip 226 can allow carrier needle 220 to enter into various tissues. In some cases, outer carrier needle 220 can be made of metals such as stainless steel or Nitinol. In some cases, outer carrier needle 220 can be a combination of a stainless steel shaft with a nitinol (or other shape memory alloy) distal tip. In some cases, outer carrier needle 220 can include flanges or textured surfaces (analogous to a cheese shredder or device used to sand or shave wood) to aid in tissue collection. In some cases, external flanges or textured surfaces can be secured prior to use by an outer sheath. In some cases, internal flanges can be actuated by an inner stylet that may be used in isolation or in conjunction with the externally placed structures. A membrane 240 can be included at a tip region (e.g., tip 226) of carrier needle 220 to seal carrier needle channel 224 and inner biopsy needle 210 within channel 224. In some cases, membrane 240 can be made of a polymer. Representative examples of suitable polymers include, without limitation, cellulose acetates, nitrates and esters, polysulfone, polyether sulfone, polyacrilonitrile, polyamide, polyimide, polyethylene, polypropylene, and polytetrafluoroethylene. Inner biopsy needle 210 can have a body 212 and a tip 216. Biopsy needle body 212 can have a channel 214 through which the needle assembly 200 can acquire biopsy tissue or cells. Biopsy needle tip 216 can have an opening 218 to collect biopsy tissue or cells. Biopsy needle 210 can be moved back and forth within needle channel 224. Biopsy needle tip 216 can allow biopsy needle 210 to access a target tissue. In some cases, biopsy needle 210 can be a metal needle that can be made of stainless steel or Nitinol.

As biopsy needle assembly 200 passes through tissues toward a target site, membrane 240 can prevent cells from non-target tissues from entering into carrier needle channel 224 to contaminate inner biopsy needle 210. When needle assembly 200 arrives at the targeted biopsy site, inner biopsy needle 210 can be moved to pierce membrane 240 to obtain target tissue or cells. In some implementations, during a biopsy procedure a pressurization device (not shown) can be used to maintain a pressure in inner biopsy needle channel 214 to a low level (e.g., vacuum) such that inner biopsy needle 210 can instantly sample target tissue or cells when biopsy needle 210 pierces membrane 240. In some implementations, a pressurization device (e.g., a syringe (not shown)) can be attached to inner biopsy needle 210 so that, after membrane 240 is pierced, target tissue or cells can be collected by actuating the pressurization device (e.g., by pulling a syringe plunger) to generate a negative pressure within inner biopsy needle channel 214.

Referring now to FIG. 3, an exemplary needle 310 can have a shaft portion 312 that can form part of the needle body and a head portion 316 that can include the needle tip. In this exemplary needle construction, shaft portion 312 is smaller in diameter than head portion 316. For example, shaft portion 312 can have a 22 gauge diameter (~0.0253 inch), and head portion 316 can have a 19 gauge diameter (~0.0359 inch). The smaller diameter of shaft portion 312 can provide flexibility to the needle body for easy maneuvering within a biopsy channel, while the larger diameter of head portion 316 can provide rigidity to the needle tip for good penetration into tissues. In some cases, the smaller diameter of shaft portion 312 can be constructed of a rigid metal to allow for effective pushability, while the larger diameter of head portion 316 can provide flexibility to facilitate broader tissue sampling. These exemplary needle constructions can be used for any of the needle assemblies providing herein, including the above inner biopsy needle, the above outer carrier needle, or both.

The needles provided herein can include a mechanism for physician-controlled variable stiffness. For example, a tensioning wire/cable that can be actuated via a triggering-type mechanism (as is used with other biopsy devices/cups) can be used to vary the stiffness as may be used in colonoscopes. Greater stiffness can be desired when pushing the needle out, but then greater flexibility can be preferred once the target is reached to allow sampling of a greater area as the more flexible needle moves back and forth. The means for providing variable stiffness (and flexibility) may be applied to the outer sheath and/or the needle itself.

Referring now to FIG. 4, an exemplary biopsy needle assembly 400 can include an inner biopsy needle 410 that can have one or more holes 411 at or near its tip end region to facilitate sampling of target tissue or cells. Needle assembly 400 can include an outer carrier needle 420 that may be similar to outer carrier needle 220 shown in FIG. 2. Outer carrier needle 420 can include a membrane 440 that seals outer carrier needle 420 at its tip end (and inner biopsy needle 410 located inside carrier needle 420) to prevent unwanted tissue or cells from contaminating inner biopsy needle 410 during needle placement into a target tissue. Membrane 440 can be pierced by inner biopsy needle 410 once needle assembly 400 reaches a desired biopsy site at a target tissue. A pressurization device (not shown) can also be used to control a pressure within inner biopsy needle channel 414 at a negative level to induce an automatic collection of target tissue or cells once sealing membrane 440 is pierced, or a pressurization device (e.g., a syringe (not shown)) can be used to manually draw target tissue or cells into biopsy needle 410 after sealing membrane 440 is pierced. The one or more holes 411 at or near the tip end region can serve as a conduit to allow passage of negative pressure from outer carrier needle 420 to the lumen of inner biopsy needle 410 once membrane 440 has been pierced.

Referring now to FIG. 5, an exemplary biopsy needle assembly 500 can include an outer carrier needle 520. Outer carrier needle 520 can be similar to outer carrier needle 220 shown in FIG. 2. An inner biopsy forceps 510 can be located inside outer carrier needle 520. Outer carrier needle 520 can include a membrane 540 that seals outer carrier needle 520 at its tip end (and inner biopsy forceps 510 inside the carrier needle 520). Membrane 540 can inhibit the translocation of unwanted tissue or cells onto inner biopsy forceps 510 during transmural needle passage, and can be pierced by inner biopsy forceps 510 when needle assembly 500 reaches a biopsy site Inner biopsy forceps 510 can have two cutting spoons or jaws 517 that are articulated at a common pivot 513 to cut target tissues.

Referring now to FIG. 6, an exemplary biopsy needle assembly 600 can include an outer carrier needle 620. Outer carrier needle 620 can be similar to outer carrier needle 220 shown in FIG. 2. An inner coring needle 610 can be located inside outer carrier needle 620. In some cases, an inner coring needle can have a corkscrew or a hardware screw design. Outer carrier needle 620 can include a membrane 640 that seals outer carrier needle 620 at its tip end (and inner coring needle 610 inside carrier needle 620). Membrane 640 can prevent inner coring needle 610 from being contaminated by tissue or cells from unintended sites during needle advancement to a target tissue Inner coring needle 610 can pierce membrane 640 to core the target tissue when needle assembly 600 reaches a desired biopsy position at the target tissue.

Referring now to FIGS. 18 and 19, an exemplary biopsy needle assembly 1800 can include an outer sheath 1820 and an inner biopsy needle 1810. Outer sheath 1820 can be configured to restrain inner biopsy needle 1810. Upon target localization, outer sheath 1820 can be retracted (or inner biopsy needle 1810 can be advanced), allowing a distal portion 1830 of inner biopsy needle 1810 to expand to a tissue collection configuration as shown in FIG. 19. In some cases, this expansion can include the uncoiling of the "memory" of a metal used to construct inner biopsy needle 1810. This expansion process (e.g., uncoiling) can allow the distal needle tip to assume a configuration possessing a larger caliber. After inner biopsy needle 1810 is advanced into the target, sheath 1820 can be re-advanced to constrain the sampled tissue. By doing so, a larger tissue sample can be obtained, and preservation of tissue architecture can be improved. The additional external force applied to the distal tip (upon sheath advancement) can serve to help capture the tissue and allow removal.

Figure 20:
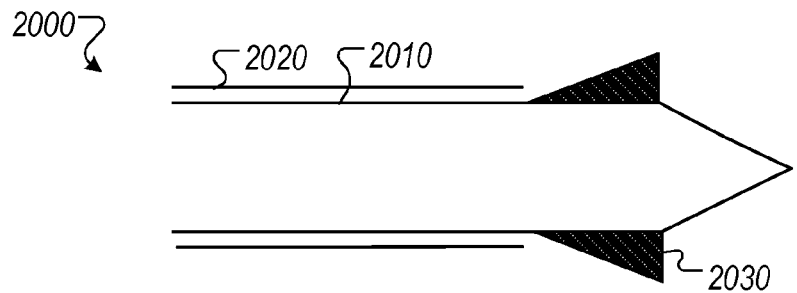
FIG. 20 shows an exemplary biopsy needle assembly having an inner biopsy needle with tissue restrainers, where the inner biopsy needle is in a deployed position.
Figure 21:
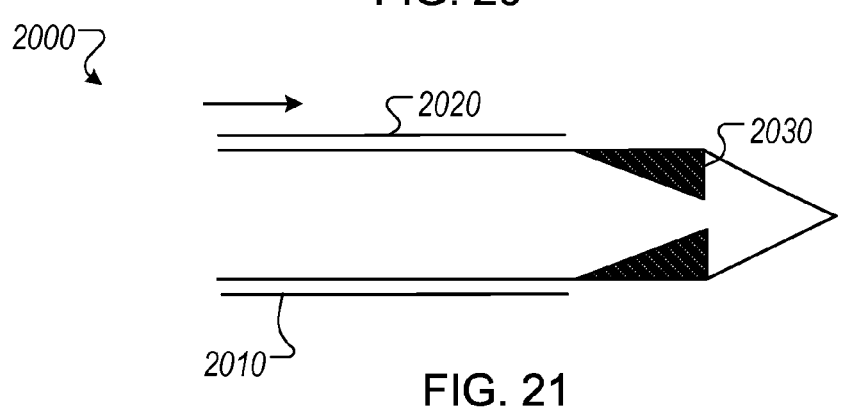
FIG. 21 shows an exemplary biopsy needle assembly having an inner biopsy needle with tissue restrainers, where the inner biopsy needle is in a retracted position.

Referring now to FIGS. 20 and 21, an exemplary biopsy needle assembly 2000 can include an outer sheath 2020 and an inner biopsy needle 2010. Outer sheath 2020 can be configured to house inner biopsy needle 2010. Upon target localization, outer sheath 2020 can be retracted (or inner biopsy needle 2010 can be advanced), allowing one or more extensions 2030 of inner biopsy needle 2010 to expand to a configuration to allow tissue collection as shown in FIG. 20. Extensions 2030 can be any appropriate shape including a wedge shape or an angled shape. After inner biopsy needle 2010 is advanced into the target tissue, sheath 2020 can be re-advanced, thereby repositioning extensions 2030 so as to constrain the sampled tissue as shown in FIG. 21. By doing so, a larger tissue sample can be obtained, and preservation of tissue architecture can be improved. The distal tip of inner biopsy needle 2010 can be constructed of a flexible metal or other material with elastic properties to allow tissue retention by compression of the distal tip.

Figure 22:
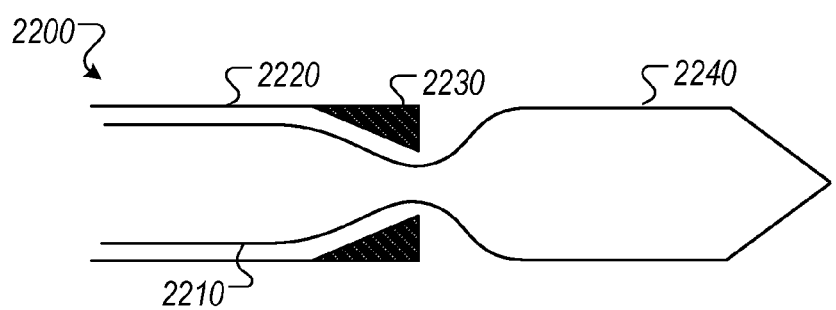
FIG. 22 shows an exemplary biopsy needle assembly having an outer sheath with tissue restrainers, where an inner biopsy needle is in a deployed position.
Figure 23:
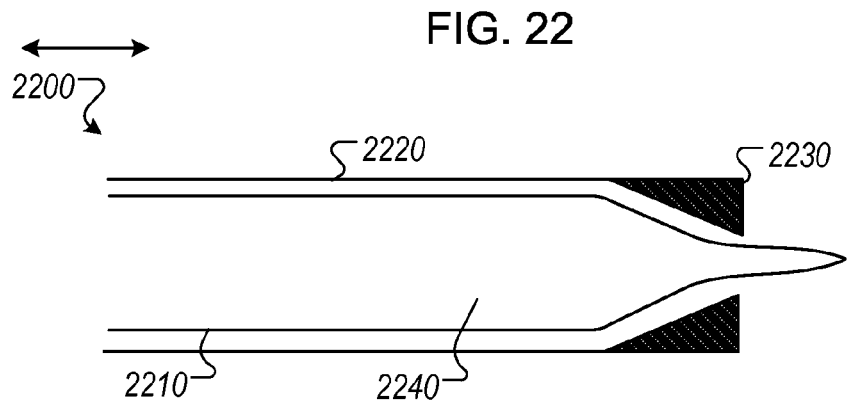
FIG. 23 shows an exemplary biopsy needle assembly having an outer sheath with tissue restrainers, where an inner biopsy needle is in a refracted position.

In some cases, extensions can be configured on an outer sheath to constrain a collected tissue sample within an inner biopsy needle. For example, as shown in FIGS. 22 and 23, an exemplary biopsy needle assembly 2200 can include an outer sheath 2220 and an inner biopsy needle 2210. Outer sheath 2220 can be configured to have one or more extensions 2230 and configured to house inner biopsy needle 2210. Upon target localization, outer sheath 2220 can be retracted (or inner biopsy needle 2210 can be advanced), allowing inner biopsy needle 2210 to move past one or more extensions 2230 to a configuration for tissue collection as shown in FIG. 22. Extensions 2230 can be any appropriate shape including a wedge shape or an angled shape. After inner biopsy needle 2210 is advanced into the target tissue, sheath 2220 can be re-advanced, thereby repositioning inner biopsy needle 2210 relative to extensions 2230 so as to constrain the sampled tissue within portion 2240 of inner biopsy needle 2210 as shown in FIG. 23. By doing so, a larger tissue sample can be obtained, and preservation of tissue architecture can be improved.

Figure 24:
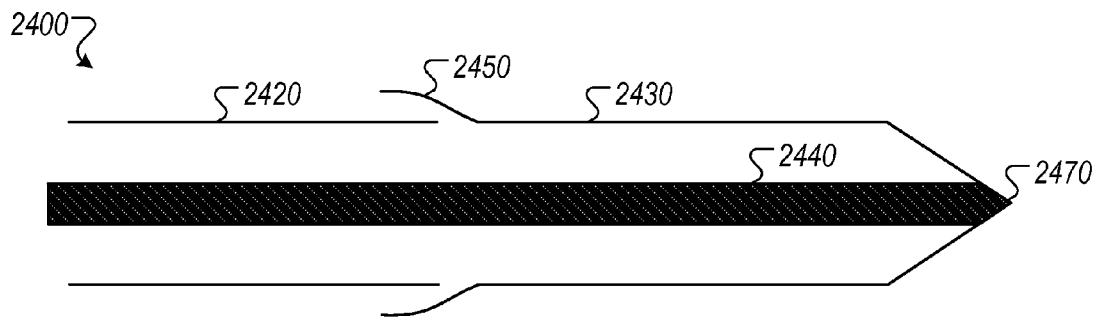
FIG. 24 shows an exemplary biopsy needle assembly having a sectional outer member (e.g., needle).
Figure 25:
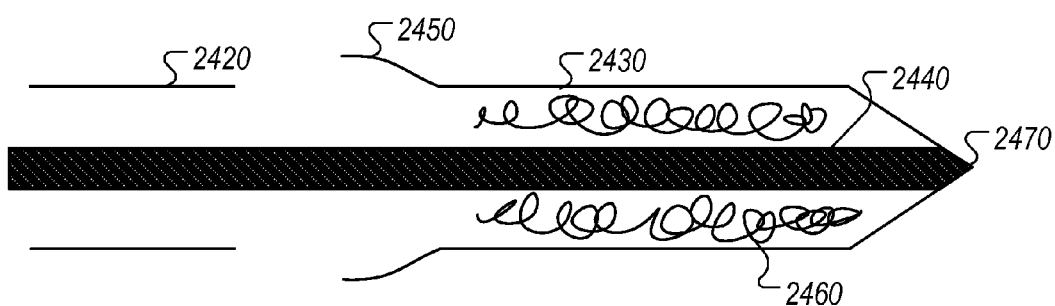
FIG. 25 shows the exemplary biopsy needle assembly of FIG. 24 in an open position.
Figure 26:
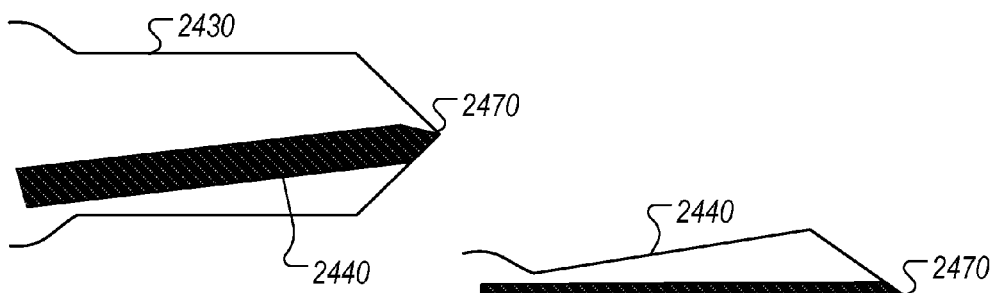
FIG. 26 shows the distal section of the exemplary biopsy needle assembly of FIG. 24 in one position.
Figure 27:
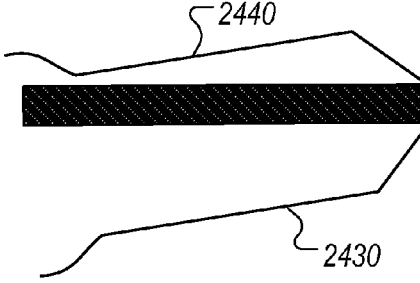
FIG. 27 shows the distal section of the exemplary biopsy needle assembly of FIG. 24 in another position.

In some cases, a biopsy needle assembly can include a central rod that is contained in a hollow needle that has at least two (e.g., two, three, four, or more) discontinuous adjacent pieces held in close proximity with a concealed cutting edge on an edge of each joint. At the biopsy site, the discontinuous pieces of the hollow needle can be separated, thereby exposing the cutting surface and allowing tissue collection. Once sampling is completed, the central rod can be pulled to align the needle components. The central rod can include an articulating element near the distal tip or may be loosely attached to a closed distal end of the hollow needle. For example, as shown in FIGS. 24 and 25, an exemplary biopsy needle assembly 2400 can include an first needle component 2420, a second needle component 2430, and an inner rod member 2440. First needle component 2420 can have a caliber that is slightly smaller than the caliber of second needle component 2430. Second needle component 2430 can include cutting edge 2450 such that a tissue sample 2460 can be collected as shown in FIG. 25. In some cases, second needle component 2430 and inner rod member 2440 can form an attachment point 2470. Attachment point 2470 can be configured to form a floating tip or loose attachment as shown in FIGS. 26 and 27.

Figure 28:
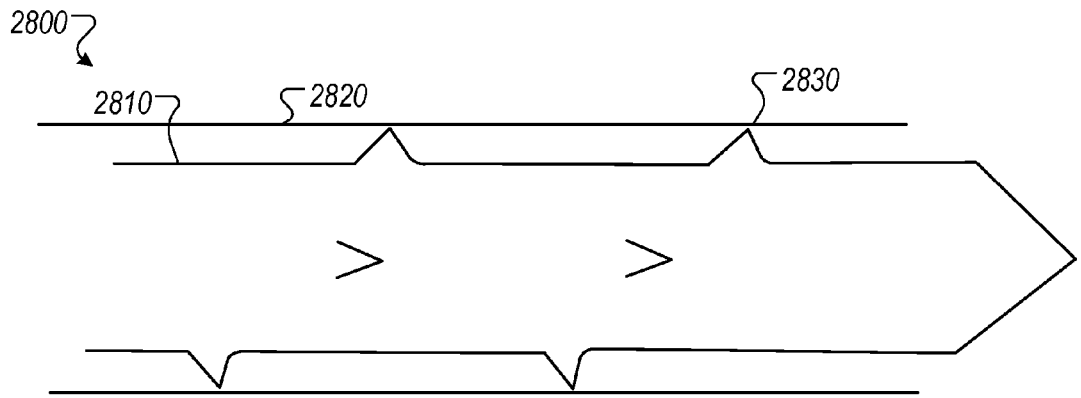
FIG. 28 shows an exemplary biopsy needle assembly having an inner biopsy needle with tissue sampling enhancers.
Figure 29:
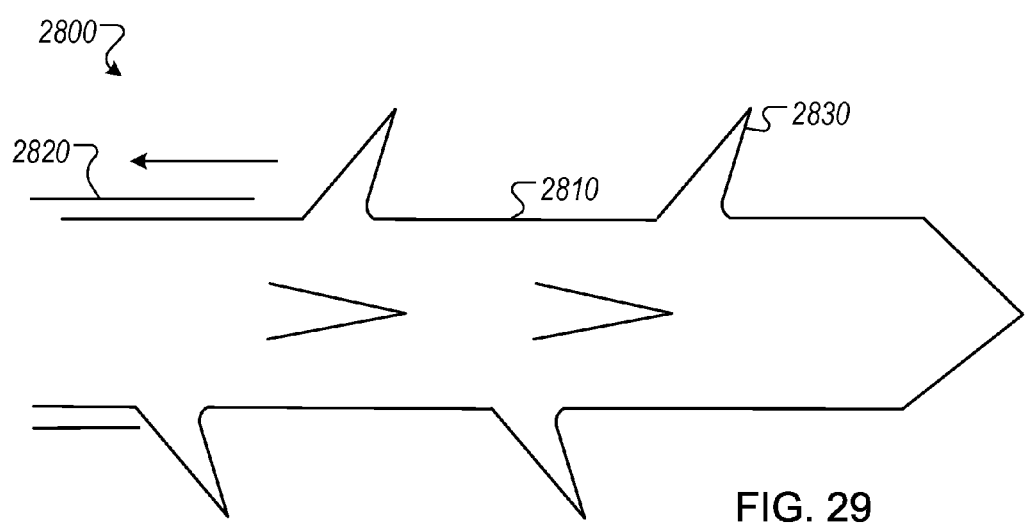
FIG. 29 shows an exemplary biopsy needle assembly having an inner biopsy needle with tissue sampling enhancers, where the inner biopsy needle is in a deployed position.

In some cases, a biopsy needle assembly provided herein can include a biopsy needle having one or more tissue sampling enhancer elements. As shown in FIGS. 28 and 29, an exemplary biopsy needle assembly 2800 can include an outer sheath 2820 and an inner biopsy needle 2810. Outer sheath 2820 can be configured to house inner biopsy needle 2810. Inner biopsy needle 2810 can include one or more tissue sampling enhancer elements 2830. Tissue collection enhancer members 2830 can be of various sizes or shapes and can be configured to enhance tissue collection through adjacent ports of the hollow inner biopsy needle 2810, through the distal tip of the hollow inner biopsy needle 2810, or may allow for captured tissue to be retained between the sheath and the outer wall of the hollow inner biopsy needle 2810 (or, for example, a solid needle). Upon target localization, outer sheath 2820 can be retracted (or inner biopsy needle 2810 can be advanced), thereby allowing tissue sampling enhancer elements 2830 to enhance tissue collection. In some cases, tissue sampling enhancer elements 2830 can expand as shown in FIG. 29.

Figures 30, 31, 32:
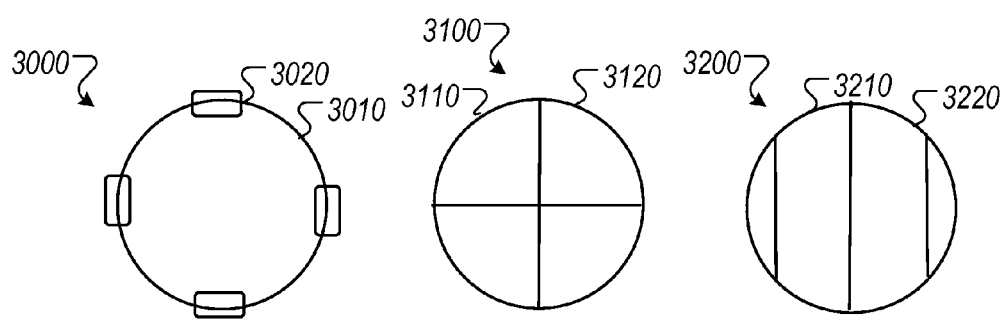
FIG. 30 shows an exemplary needle configuration.
FIG. 31 shows an exemplary needle configuration.
FIG. 32 shows an exemplary needle configuration.

In some cases, a needle or stylet provided herein can be steerable. For example, a steering mechanism such as those described elsewhere or available commercially (Sears and Dupont, Proc. Of the 2006 IEEE/RSJ International Conf. on Intelligent Robots and Systems, Beijing, China, Oct. 9-15 (2006), pp. 2850-2856; Seeker Steerable Biopsy Needle™ from PneumRX (Mountain View, Calif.); or U.S. Pat. No. 7,662,128) can be used to steer a distal tip. In some cases, the tip portion of a needle or stylet can include one or more stiffeners. Such stiffeners can be arranged in any appropriate configuration. For example, as shown in FIG. 30, needle or stylet 3000 can include a tip region made of a first material 3010 and a region made of a second material 3020. Second material 3020 can be stiffer than first material 3010. As shown in FIG. 31, needle or stylet 3100 can include a tip region divided into quarters (or halves, thirds, etc.) with some regions made of a first material 3110 and others made of a second material 3120. Second material 3120 can be stiffer than first material 3110. As shown in FIG. 32, needle or stylet 3200 can include a tip region made of layers of a first material 3210 and a second material 3220. Second material 3220 can be stiffer than first material 3210.

Figure 33:
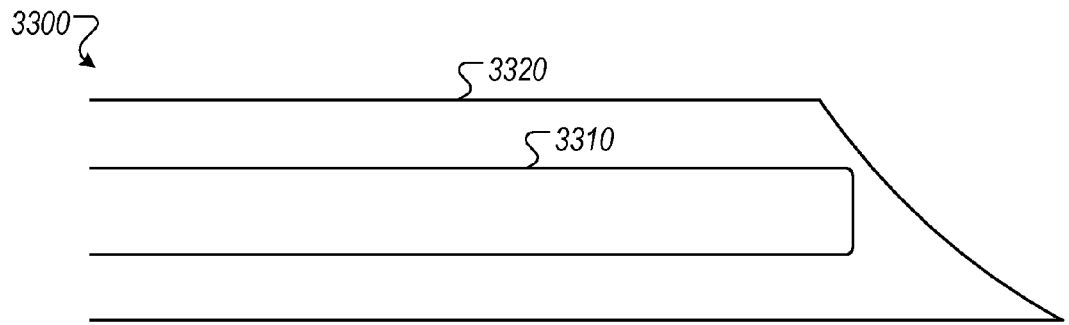
FIG. 33 shows an exemplary biopsy needle assembly having an inner biopsy needle.
Figure 34:
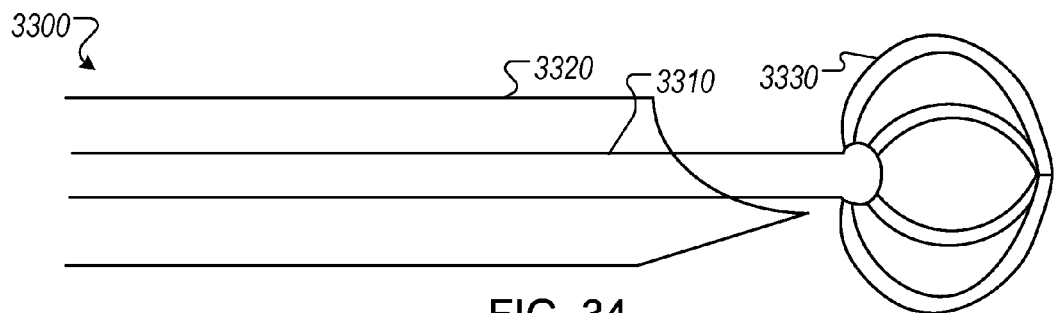
FIG. 34 shows an exemplary biopsy needle assembly having an inner biopsy needle, where the inner biopsy needle is in a deployed position.

In some cases, a biopsy needle assembly provided herein can include a hollow needle or sheath that houses an inner stylet that is expandable. As shown in FIGS. 33 and 34, an exemplary biopsy needle assembly 3300 can include an outer needle 3320 and an inner stylet 3310. Outer needle 3320 can be configured to house inner stylet 3310. Inner stylet 3310 can include expanding region 3330 at its distal end portion. Expanding region 3330 can be of various sizes or shapes following expansion and can be configured to enhance tissue collection. Upon delivery to a target location, inner stylet 3310 can expand to an expanded configuration and can be rotated or moved. For example, inner stylet 3310 can be moved in a manner that helps to disrupt or destroy a portion of the target site. Stylet 3310 and/or needle 3320 can include aspiration ports (e.g. for aspiration of fluid or tissue samples) and/or fluid delivery ports for delivery of saline, therapeutic agents, or other fluids to the target site or any position along the delivery path. The expandable configuration of inner stylet 3310 can aid in holding cysts or tissue. In some cases, the expandable configuration of inner stylet 3310 can aid in maintaining the position of the stylet within, e.g., a bile duct or pancreatic duct.

Figure 35:
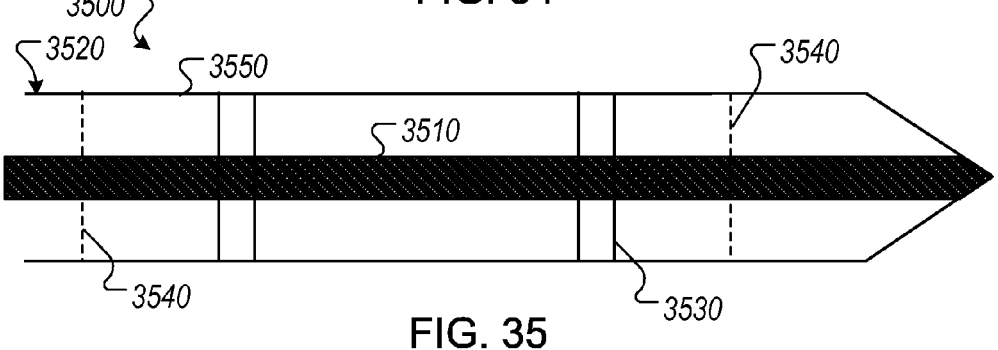
FIG. 35 shows an exemplary biopsy needle assembly having a sectional outer sheath.
Figure 36:
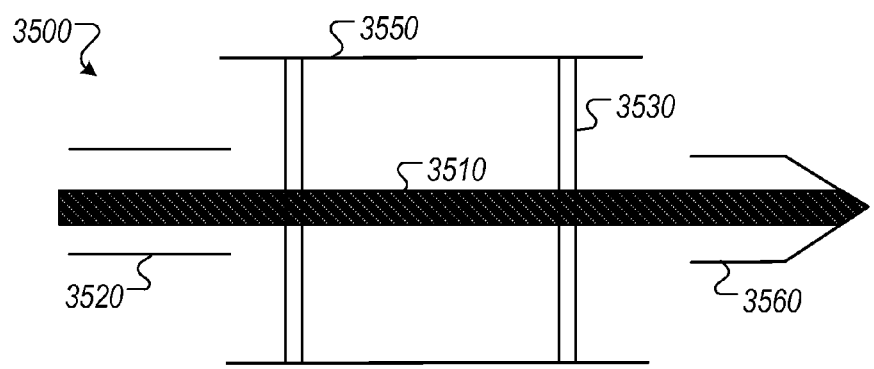
FIG. 36 shows an exemplary biopsy needle assembly having a sectional outer sheath in a deployed position.

In some cases, a biopsy needle assembly provided herein can include a hollow needle or sheath having a section configured to move outward from a central axis of the needle or sheath. As shown in FIGS. 35 and 36, an exemplary biopsy needle assembly 3500 can include an outer needle 3520 and an inner stylet 3510. Outer needle 3520 can be configured to house inner stylet 3510. Outer needle 3520 can include separation points 3540 that can allow needle section 3550 to move outward relative to other sections of the outer needle (e.g., a proximal region of outer needle 3520, a distal region 3560 of outer needle 3520, and/or radial regions). Supports 3530 can be included to connect needle section 3550 to inner stylet 3510. Supports 3530 can be made of an expandable material to aid in the outward movement of needle section 3550 as shown in FIG. 36. Upon delivery to a target location, inner stylet 3510 and/or supports 3530 can expand to an alternate configuration to move needle section 3550 outward. In some cases, needle section 3550 can be semi-lunar components of the needle wall. Moving needle section 3550 outward can lead to several pieces of the wall that extend further from the center and leave spaces between the semi-lunar components. As the device is rotated or moved, a tissue sample can be collected. In some cases, stylet 3510 and/or needle 3520 can include aspiration ports (e.g., for aspiration of fluid or tissue samples) and/or fluid delivery ports for delivery of saline, therapeutic agents, or other fluids. In some cases, the device can be moved in a manner that helps to disrupt or destroy a portion of the target site.

The biopsy needle assemblies described herein can be used in various needle biopsy systems including endoscopic ultrasound-guided fine needle aspiration systems. In the endoscopic ultrasound-guided fine needle aspiration systems, the biopsy needle assemblies described herein can be manipulated by a handle piston in a handle. The handle piston can be locked or unlocked by means of a button or screw. The needle assemblies can be supported by a sheath that may be connected to the handle. In some cases, the sheath can be a metal spiral sheath. In some cases, the sheath can be made of a metal ring that may be coated with Teflon. In some cases, the sheath can be made entirely of Teflon or other suitable plastics. The handle can be connected to an endoscope using, e.g., a Luerlock. When the handle is connected to the endoscope, the sheath can extend a few millimeters (e.g., 4-5 mm) out of a distal outlet of a working channel of the endoscope.

Existing needle biopsy systems typically ramp up negative pressure to a required level when the needle reaches a desired biopsy site. This may cause the needle to move thereby potentially causing unwanted bleeding. The needle biopsy systems provided herein can allow a predetermined low pressure level to pre-exist within the biopsy systems prior to needle advancement. Once the needle reaches a desired location in a target tissue, an operator can release the pressure level using a button, trigger, stopcock, or a similar device.

Referring now to FIG. 7, an exemplary needle biopsy system 700 can control the actuation of a negative pressure during a biopsy procedure. Biopsy system 700 can include a monoject syringe (not shown) that can have a valve 710, e.g., stopcock. Inside the monoject syringe, a negative pressure can be maintained when valve 710 is in a closed position. Biopsy system 700 can also include a handle 720 having a piston 724 that can advance or retract a needle 730 for biopsy.

Needle 730 can be a biopsy needle described herein. In some cases, needle 730 can be a standard existing biopsy needle. Handle 720 can be connected to the monoject syringe such that handle 720 and the syringe can be in fluid communication when valve 710 is in an open position. Valve 710 can be attached to handle piston 724 by a connector 726 (e.g., a removable string or collar) so that advancement of handle piston 724 to penetrate needle 730 into a target tissue would cause valve 710 to open gradually. This would allow the negative pressure level maintained in the monoject syringe to permeate into the interior of the handle (and the interior of the needle) so as to facilitate collection of target tissue or cells. Handle 720 can include a screw 728 to lock handle piston 724 in position when needle 730 reaches a desired biopsy position. In some cases, the biopsy system can adjust the distance between the needle tip and the target tissue without moving the handle piston.

Figure 12:
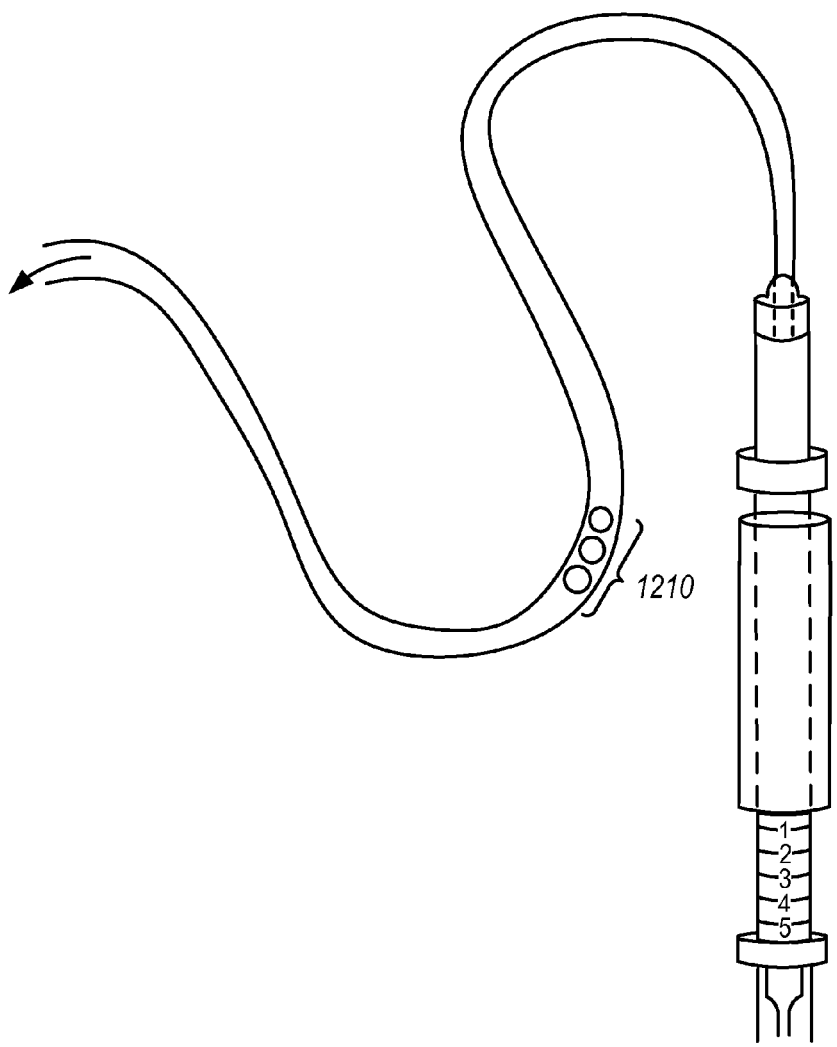
FIG. 12 shows an exemplary needle biopsy system to control negative pressure actuation using holes present in the tube.

In some cases, the pressure of a needle biopsy system provided herein can be controlled using a hole or series of holes that are located in the system (e.g., in the handle, shaft, or tubing). For example, a physician can cover the hole or holes with a thumb or finger(s) or foot-activated mechanism to close the system, thereby allowing the physician to rapidly and as needed activate or remove the delivery of negative pressure. Such a mechanism can be used to adjust quantitatively the amount of pressure delivered to the needle. As shown in FIG. 12, holes 1210 can be located in the tube, which can be flexible such that the physician can cover the holes using the same hand that holds the handle of the needle biopsy system or another device (e.g., an endoscope). In some cases, a nurse, assistant, or other team member can actuate pressure delivery. The multiple holes can allow for variable levels of suction and can be of varying (e.g. increasing or decreasing) diameters. The holes are of sufficient size to allow suction or aspiration without allowing negative pressure to be applied to the needle unless the system is closed by covering one or more of the holes. Such design can allow for the rapid delivery and cessation of negative pressure to the needle system.

In some cases, and with reference to FIG. 13, holes 1210 can be covered with slider 1310. In some cases, slider 1310 can be a sleeve that surrounds tube 925, or can be a flap that partially covers tube 925. The flap can be slidably engaged with tube 925 via tracks or guides located on the outer surface of tube 925. In some cases, slider 1310 can include ratchets 1330 or an audible indicator to provide a physical with a indication of slider movement over or off of (e.g., opening or closing) one or more holes.

In some cases, tube 925 can be designed to control the internal pressure. For example, tube 925 can be in a flattened configuration such that the tube is in a closed position as the default position (FIG. 15), and can be opened by squeezing or pinching the tubing walls (FIG. 16), thereby converting tube 925 into an open position and allowing negative pressure to flow through the system.

Referring now to FIG. 8, an exemplary needle biopsy system 800 can control the actuation of a negative pressure during a biopsy procedure. Biopsy system 800 can include a handle 820 having a piston 824 that can advance or retract a needle 830 for biopsy. A membrane 840 can be located inside handle 820 that seals the handle channel to separate needle 830 from a negative pressure level that is regulated by, e.g., a monoject syringe (not shown). Biopsy system 800 can also include a trocar 850 that resides inside handle 820. Trocar 850 can be attached to handle piston 824 so that the movement of piston 824 would simultaneously advance needle 830 to penetrate a target tissue and trocar 850 to pierce membrane 840, thereby releasing the negative pressure level to assist sampling of target tissue or cells.

Referring now to FIG. 9, system 900 can include a monoject syringe 910 connected to a needle biopsy system 920 via tube 925. Monoject syringe 910 can be used to pressurize needle biopsy system 920. Monoject syringe 910 can create a negative pressure within biopsy system 920 when a plunger 915 of syringe 910 is pulled. Other pressurizing methods can also be used. For example, a suction gun or a wall mounted pressure unit can be used to introduce a low pressure in a needle biopsy system. The pressurization of the biopsy system can be activated by an automated triggering device in combination with a membrane or plug as described herein, or can be activated manually by an operator by, e.g., pressing down a foot pedal. In some cases, the negative pressure level created in the biopsy system can be −10, −20, −30 psi, or lower or any values in between.

In some cases, a system having holes can be used in combination with a membrane or plug, or can be used without a membrane or plug. Likewise, an inflator 1010 of FIG. 10 can be used with or without a membrane or plug.

Figure 17:
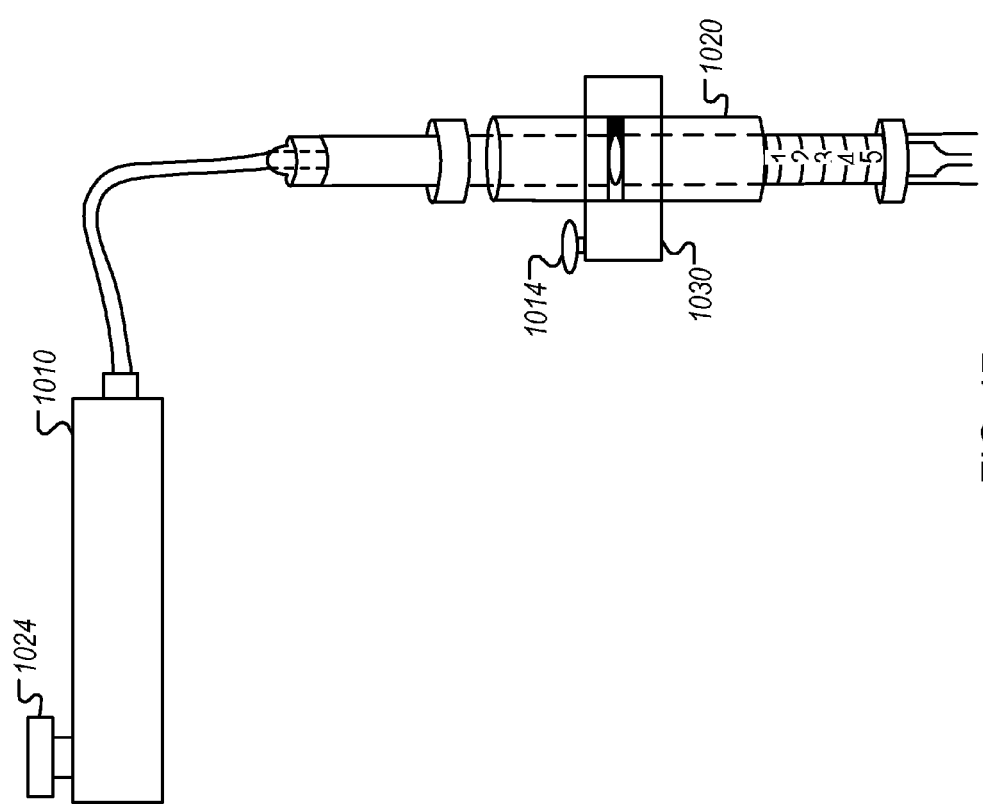
FIG. 17 shows an exemplary use of an inflator for controlled release of negative pressure.

FIG. 10 shows an exemplary device 1000 that can be used to control the release of a negative pressure. Using this device 1000, a negative pressure can be held within an inflator 1010 until released by actuating slider member 1030. Inflator 1010 can be attached to a biopsy system handle 1020 that can have a button 1014 that can allow an operator to release controllably the negative pressure when desired. Inflator 1010 can include an illuminated pressure gauge 1024 that can allow an operator to monitor the pressure level. Inflator 1010 and illuminated pressure gauge 1024 can be attached to an endoscope, a biopsy system handle, or can be freely moveable (FIG. 17). This exemplary device 1000 can be used to regulate the pressure in a needle biopsy system. Device 1000 also can be used generally to allow an operator to actuate pressure release while using an endoscope, e.g., for balloon inflation.

Figure 11:
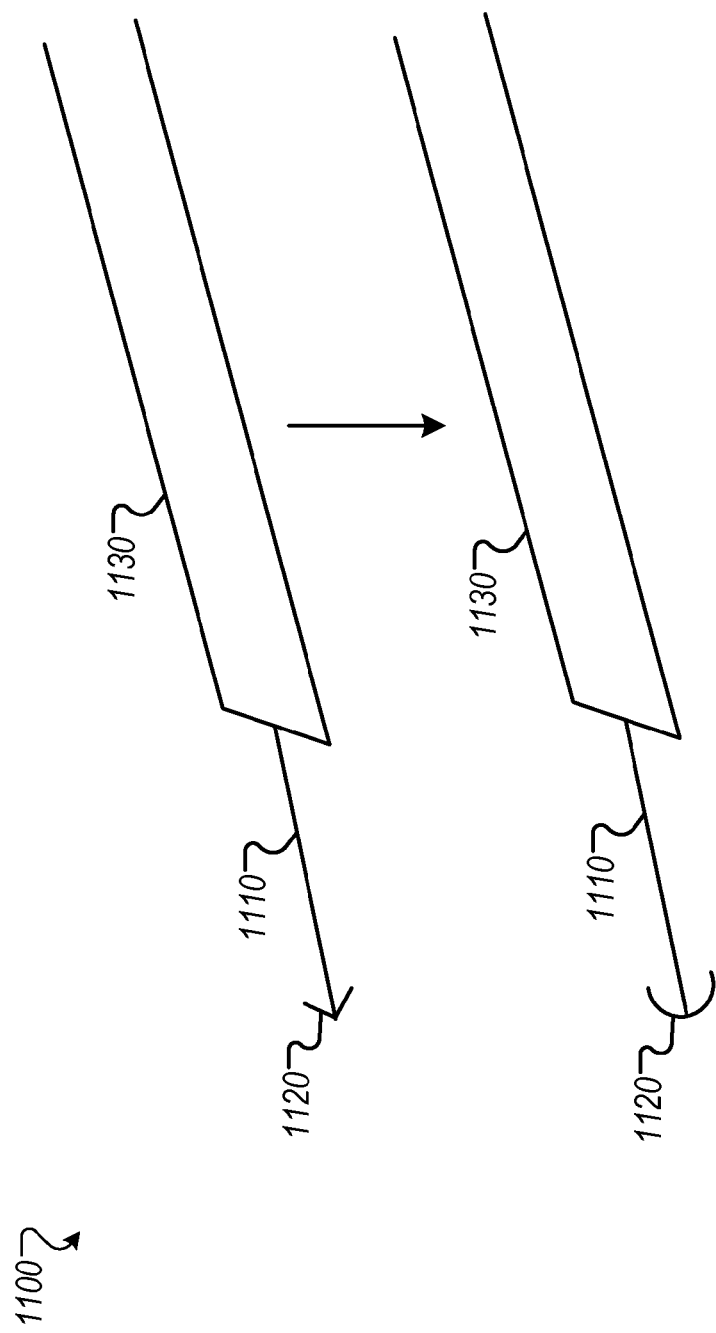
FIG. 11 shows an exemplary biopsy umbrella cable made of shape material.

Referring now to FIG. 11, an exemplary umbrella biopsy cable 1100 can include an arm 1110 and an umbrella tip 1120. Either arm 1110 or umbrella tip 1120 or both can be made of Nitinol or other shape memory alloys. When biopsy cable 1100 is inserted into a human tissue, arm 1110 and/or umbrella tip 1120 can change its shape and/or size (e.g., can be collapsed, expanded, bent, shorten, elongated, or the like) due to the variations in, for example, temperature or chemical environment. This can allow biopsy cable 1100 to be deployed from a needle 1130 in different orientations.

The biopsy systems provided herein can be used in various biopsy procedures including endoscopic ultrasound-guided fine needle aspiration. When using the biopsy systems provided herein in typical endoscopic ultrasound-guided fine needle aspiration procedures, the sheath can first be inserted into the working channel of the endoscope with the handle piston locked and the needle assembly retracted. The handle with the lock can then be attached onto the endoscope working channel. When the sheath is visible at the distal end of the working channel, the needle assembly can be advanced until the biopsy direction can be estimated, and the target tissue can be reached. The needle assembly can then be advanced into the target tissue under full real-time ultrasound control. Upon reaching the desired needle position in the target tissue, the stylet can push the plug out of the needle tip or the inner biopsy device (e.g., coring or non-coring needle, forceps) can puncture the membrane open. The target tissue or cells can then be automatically sampled if the biopsy systems have been maintained at a negative pressure, or a pressurization device (e.g., a syringe) connected to the needle can be actuated (e.g., by pulling a syringe plunger) to create a low pressure to facilitate tissue or cells collection. The needle assembly can then be removed by disconnection from the inlet of the endoscope. After the biopsy, the sample tissue or cells can be transferred to an appropriate specimen device (e.g., a container or a slide) by air with the syringe or by re-introducing the stylet into the needle and moving the stylet forward.

In some cases, the biopsy systems provided herein can include a wire straightening device that can be a stand-alone item included in a kit or that can be included as part of a handle or needle design. As several biopsies are often taken on the same patient during the same procedure, the wire-straightening device can allow the physician to remove kinks and bends that often occur. The wire straightening device can have a two, three, or more roller design similar to those used in electrical and construction applications. In some cases, the wire straightening device can be a longitudinally split cylinder or "c" shaped channel, which is optionally lined with rubber or other protective lining. The wire straightening device can be configured such that a wire can be snapped into and pulled through, thereby straightening the wire. The wire straightening device can be designed to allow straightening of the inner needle itself and/or the entire needle assemble that includes both the inner needle and outer sheath.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A biopsy needle assembly comprising:
   a needle having a body portion and a tip portion, said body portion having a channel and said tip portion having an opening, wherein said channel and said opening are configured to acquire a tissue biopsy;
   a plug located within said opening at said tip portion and configured to seal said channel;
   a slideable stylet located within said channel at said body portion and configured to push said plug out of said opening, and
   a pressurization device configured to regulate a pressure within said channel to a negative level during a biopsy procedure.

2. The needle assembly of claim 1, wherein the pressurization device comprises a syringe, a suction gun, or a wall mounted pressure unit.

3. A method of obtaining a tissue biopsy comprising:
   providing a biopsy needle assembly comprising:
   a needle having a body portion and a tip portion, said body portion having a channel and said tip portion having an opening;
   a plug located within said opening at said tip portion and configured to seal said channel; and
   a slideable stylet located within said channel at said body portion and configured to push said plug out of said opening;
   advancing said biopsy needle assembly to a desired biopsy site;
   actuating said slideable stylet to push said plug out of said needle; and
   applying a negative pressure within said channel to acquire a tissue biopsy through said opening and said channel.

4. A biopsy needle assembly comprising:
   an outer carrier needle having a body portion and a tip portion, said body portion having a channel and said tip portion having an opening;
   a membrane located within said opening at said tip portion and configured to seal said channel; and
   a slideable inner biopsy device located within said channel at said body portion and configured to pierce said membrane.

5. The needle assembly of claim 4, wherein said inner biopsy device comprises an inner biopsy needle having a body portion and a tip portion, wherein said body portion of said inner biopsy needle has a channel and said tip portion of said inner biopsy needle has an opening, and wherein said inner biopsy needle is configured to acquire a tissue biopsy.

6. The needle assembly of claim 5, wherein said body portion of said outer carrier needle has a smaller diameter than said tip portion of said outer carrier needle, and wherein said body portion of said inner biopsy needle has a smaller diameter than said tip portion of said inner biopsy needle.

7. The needle assembly of claim 5, wherein said inner biopsy needle includes one or more holes to assist tissue biopsy acquisition.

8. The needle assembly of claim 5 further comprising a pressurization device configured to regulate a pressure within said channel of said inner biopsy needle to a negative level during a biopsy procedure.

9. The needle assembly of claim 8, wherein said pressurization device comprises a syringe, a suction gun, or a wall mounted pressure unit.

10. The needle assembly of claim 4, wherein said inner biopsy device comprises an inner biopsy forceps configured to cut a target tissue.

11. The needle assembly of claim 4, wherein said inner biopsy device comprises an inner coring needle configured to core a target tissue.

12. A method of obtaining a tissue biopsy comprising:
    providing a biopsy needle assembly comprising:
    an outer carrier needle having a body portion and a tip portion, said body portion having a channel and said tip portion having an opening;
    a membrane located within said opening at said tip portion and configured to seal said channel; and
    a slideable inner biopsy device located within said channel at said body portion and configured to pierce said membrane;
    actuating said slideable inner biopsy device to pierce said membrane; and
    acquiring a tissue biopsy using said inner biopsy device.

13. A needle biopsy system comprising:
    a pressurization device having a channel and configured to create a negative pressure within said channel;
    a handle having a channel and a piston configured to advance or retract a biopsy needle; and
    a valve configured to separate said channel of said pressurization device and said channel of said handle when the valve is a closed position and to allow fluid communication between said channel of said pressurization device and said channel of said handle when the valve is in an open position;
    wherein said valve is attached to said handle piston so that an advancement of said piston simultaneously causes an advancement of said biopsy needle and a gradual opening of said valve.

14. The biopsy system of claim 13, wherein said pressurization device comprises a syringe, a suction gun, or a wall mounted pressure unit.

15. The biopsy system of claim 13, wherein said biopsy needle comprises a biopsy needle assembly comprising a needle having a plug located at a tip end to seal said needle and a slideable stylet located inside said needle to push said plug out of said needle.

16. The biopsy system of claim 13, wherein the biopsy needle comprises a needle assembly comprising an outer carrier needle having a membrane located at a tip end to seal said outer carrier needle and a slideable inner biopsy device located inside said outer carrier needle to pierce said membrane.

17. The biopsy system of claim 16, wherein said slideable inner biopsy device comprises an inner biopsy needle configured to acquire a tissue biopsy.

18. The biopsy system of claim 17, wherein said outer carrier needle comprises a body portion and a tip portion that has a larger diameter than said body portion of said outer carrier needle, and wherein said inner biopsy needle has a body portion and a tip portion that has a larger diameter than said body portion of said inner carrier needle.

19. The biopsy system of claim 17, wherein said inner biopsy needle includes one or more holes to facilitate tissue sampling.

20. The biopsy system of claim 16, wherein said inner biopsy device comprises an inner biopsy forceps configured to cut a target tissue.

21. The biopsy system of claim 16, wherein said inner biopsy device comprises an inner coring needle configured to core a target tissue.

* * * * *